United States Patent
Lee et al.

(10) Patent No.: US 7,846,967 B2
(45) Date of Patent: Dec. 7, 2010

(54) COSMETIC COMPOSITION FOR SKIN WHITENING COMPRISING SENKYUNOLIDE A AS ACTIVE INGREDIENT

(75) Inventors: Kang-Tae Lee, Chunan-shi (KR); Jung-No Lee, Chungcheongnam-do (KR); Jee-Hean Jeong, Suwon-shi (KR); Young-Jin Lee, Chunan-shi (KR); Seung-Ji Lee, Chunan-shi (KR)

(73) Assignee: Coreana Cosmetics Co., Ltd., Chungcheongnam-do (KR)

( * ) Notice: Subject to any disclaimer, the term of this patent is extended or adjusted under 35 U.S.C. 154(b) by 1289 days.

(21) Appl. No.: 11/389,284

(22) Filed: Mar. 27, 2006

(65) Prior Publication Data

US 2006/0165619 A1 Jul. 27, 2006

Related U.S. Application Data

(62) Division of application No. 10/353,010, filed on Jan. 29, 2003, now abandoned.

(30) Foreign Application Priority Data

Oct. 29, 2002 (KR) ............................... 2002-66050

(51) Int. Cl.
*A01N 43/08* (2006.01)
*A61K 31/34* (2006.01)
*C07D 317/08* (2006.01)

(52) U.S. Cl. ...................................... 514/470; 549/229

(58) Field of Classification Search ................. 514/470; 549/229

See application file for complete search history.

(56) References Cited

U.S. PATENT DOCUMENTS 6,326,006 B1   12/2001   Sato et al.

FOREIGN PATENT DOCUMENTS

JP        56092208 A    *   7/1981
JP        07017845 A    *   1/1995

OTHER PUBLICATIONS

Li Shao-Bai; "Syntheses of ligustilide and (+/−)-sedanenolide"; Gaodeng Xuexiao Huaxue Xuebao, 1995, vol. 16, No. 9, p. 1420-1422; article ordered, STN reference to article included.*
Kenney, J.A. "Melanin Pigmentation" Journal of the National Medical Association, Sep. 1961, vol. 53, No. 5, pp. 447-455.*

* cited by examiner

*Primary Examiner*—Sreeni Padmanabhan
*Assistant Examiner*—Kendra D Carter
(74) *Attorney, Agent, or Firm*—Nixon & Vanderhye P.C.

(57) ABSTRACT

The present invention relates to cosmetic compositions and more particularly to skin-whitening cosmetic compositions comprising senkyunolide A as an active ingredient. The present invention discloses the novel inhibitory function of senkyunolide A isolated from *Cnidium officinale* and *Ligusticum chuanxiong* on the melanocyte-stimulating hormone (MSH), and provides MSH-inhibitory compositions and skin-whitening cosmetic compositions comprising the senkyunolide A. The compositions of the present invention show significantly enhanced skin-whitening effect owing to its efficient inhibition of MSH even in lower concentration.

4 Claims, No Drawings

COSMETIC COMPOSITION FOR SKIN WHITENING COMPRISING SENKYUNOLIDE A AS ACTIVE INGREDIENT

The present application is a divisional of Ser. No. 10/353,010, filed Jan. 29, 2003 now abandoned, which claims benefit of Republic of Korea 2002-66050, filed Oct. 29, 2002, the entire contents of each of which is hereby incorporated by reference in this application.

BACKGROUND OF THE INVENTION

1. Field of the Invention

The present invention relates to a cosmetic composition and more particularly, to a cosmetic composition for skin whitening comprising senkyunolide A as an active ingredient and its applications.

2. Description of the Related Art

Colors of human skin, hair and iris are ascribed to melanin, keratin and hemoglobin. The melanin has been considered as a pivotal factor for skin color and the color of skin is determined depending on the amount, disposition and distribution of melanin.

The major factor of skin-darkening is over-expression of melanin. UV-irradiated epidermal keratinocytes secrete melanin-inducing factors resulting in synthesis of melanin from activated dermal melanocytes and the secreted melanin on epidermis pigments the skin.

Detail mechanism of melanin synthesis has been investigated. In an activated melanocyte, tyrosinase converts tyrosine into dopaquinone and its oxidized derivative, dopachrome, is consecutively oxidized into 5,6-dihydroxyindole (DHI) and 5,6-dihydroxyindole-2-carboxylic acid (DHICA). The final copolymerization of the DHI and DHICA forms melanin.

Currently, most inhibitors of melanin synthesis target the tyrosinase. Well-known tyrosinase inhibitors are kojic acid, albutin, hydroquinone, vitamin C and extracts of various natural materials.

Recent years saw dramatic investigations both in terms of interrelation of keratinocyte and melanocyte, and cytokines secreted by keratinocytes. Among them, the roles of endothelin, prostaglandin, nitric oxide and melanocyte-stimulating hormone (MSH) in activation of melanocytes leading to melanogenesis have been reported several times.

Therefore, the present inventors have been endeavored to alleviate the melanin-inducing stimuli such as UV irradiation and to inhibit the UV-derived physiological activity and synthesis of melanin-inducing factors. In particular, the present inventors gave a due investigation on candidate substances enabling to inhibit melanin synthesis induced by melanocyte-stimulating hormone (MSH).

α-melanocyte stimulating hormone (αMSH) expressed by UV irradiation or pregnancy binds to its receptor on melanocyte leading to increase of melanin via activation of melanocyte, tyrosinase and melanocyte dendrite. Consequently, it is highly probable to gain skin-whitening effect and alleviation of pigmentation by inhibiting αMSH. For that reason, the need of inhibitors for α MSH has been highly rising in the art.

SUMMARY OF THE INVENTION

Having made intensive investigations on inhibition of melanocyte stimulating hormone (MSH) to provide inhibition of melanin synthesis and ultimately to achieve skin-whitening effect, the present inventors have identified the novel MSH-inhibitory function of senkyunolide A, a kind of phthalide extracted from *Cnidium officinale* and *Ligusticum chuanxiong* and observed an improved skin-whitening effect of cosmetic compositions comprising the senkyunolide A.

Accordingly, it is an object of this invention to provide an inhibitory composition against MSH induced melanogenesis.

It is another object of this invention to provide a cosmetic composition showing skin-whitening effect.

Other objects and advantages of the present invention will become apparent from the detailed description to follow taken in conjugation with the appended claims and drawings.

DETAILED DESCRIPTION OF THIS INVENTION

In one aspect of this invention, there is provided a cosmetic composition for skin whitening comprising: (a) a senkyunolide A as an active ingredient; and (b) a cosmetically acceptable carrier.

In another aspect of this invention, there is provided a composition for inhibiting melanocyte-stimulating hormone (hereinafter, referred to as "MSH") comprising senkyunolide A as an active ingredient.

In an effort to follow the above need in the art, the present inventors had strived to develop inhibitors of MSH and finally found not only the extract of *Cnidium officinale* and *Ligusticum chuanxiong* with inhibitory activity to MSH but also the enhanced skin-whitening effect of cosmetic compositions comprising such extract, which is disclosed in Korean Patent Application NO.2002-25213, the teaching of which is incorporated herein by reference in its entity.

As a proceeding investigation, the present inventors have endeavored to isolate an active ingredient from the extract of *Cnidium officinale* and *Ligusticum chuanxiong* and identified the MSH-inhibitory effect of senkyunolide A among various substances. This activity of senkyunolide A is conspicuous owing to its unprecedented discovery of the novel function.

Senkyunolide A (3-butyl-6,7-dihydrophthalide), a naturally occurring phthalide, is represented by the following formula I:

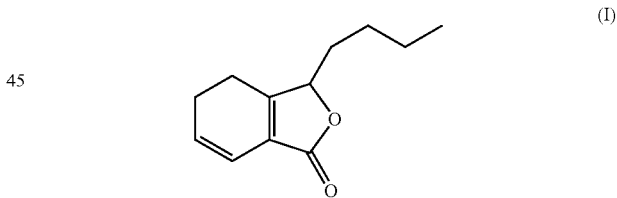

(I)

According to a preferred embodiment of the invention, the senkyunolide A used has been isolated from *Cnidium officinale* or *Ligusticum chuanxiong*, which are perennial herbs of Umbelliferae.

Various phthalides are contained in the herbs. In particular, *Cnidium officinale* comprises ligustilide, butylidenephthalide, sekyunolide A and sekyunonlide H (Kobayashi S. et al., Antiproliferative effects of the traditional Chinese medicine shimotsu-to, its component Cnidium rhizome and derived compounds on primary cultures of mouse aorta smooth muscle cells. *Jpn J Pharmacol.* 1992. 60(4):397-401) and *Ligusticum chuanxiong* comprises 3-butylphthaldie, 3-butylidenephthalide, 3-butylidene-4-hydroxyphthalide, neocnidilide, Z-ligustilide, E-ligustilide, senkyunolide A, senkyunolide F, senkyunolide H and senkyunolide I (Li H X. et al., Separation and identification of the phthalic anhydride derivatives of *Ligusticum chuanxiong* Hort by GC-MS, TLC, HPLC-DAD and HPLC-MS. 2002. *J Chromatogr Sci.* 40(3): 156-61).

Among them, the senkyunolide A of the invention showed a novel MSH-inhibitory activity and more enhanced skin-whitening effect than conventional whitening agents showing inhibition of tyrosinase activity.

Furthermore, the purified senkyunolide A according to the present invention is a potential candidate for skin-whitening agent since its $IC_{50}$ is much lower than extract of *Cnidium officinale* or *Ligusticum chuanxiong*.

According to the present invention, although various organs and tissues such as roots, foliage, flowers, stems, fruitage and seeds from *Cnidium officinale* or *Ligusticum chuanxiong* can be employed, the most preferred source is roots.

In a preferred embodiment, senkyunolide A of the present invention is isolated from the extract of *Cnidium officinale* or *Ligusticum chuanxiong*. The extract of *Cnidium officinale* or *Ligusticum chuanxiong* may be acquired using various extraction solvents, e.g. (a) water, (b) anhydrous or hydrous lower alcohol containing 1-4 carbon atoms (methanol, ethanol, propanol, butanol, etc.), (c) mixture of the lower alcohol and water, (d) acetone, (e) ethyl acetate, (f) chloroform, (g) 1,3-butyleneglycol, (h) butyl acetate. More preferable extraction solvent for this invention is the hydrous lower alcohol, and the most preferable solvent is ethanol. Furthermore, it is apparent to one skilled in the art that other conventional solvents may be employed for substantially similar isolating efficiency.

Senkyunolide A according to the present invention can be isolated and purified from *Cnidium officinale* or *Ligusticum chuanxiong* using the known methods in the art. For instance, the isolation and purification may employ gas chromatography (GC), head space gas chromatography (HSGC), liquid chromatography (LC), high performance liquid chromatography (HPLC) and thin layer chromatography (TLC).

Moreover, the present invention may employ senkyunolide A prepared by not only isolating from *Cnidium officinale* or *Ligusticum chuanxiong* extract but also synthesizing chemically.

According to the preferred embodiment of the present invention, the effective amount of senkyunolide A in cosmetic composition is 0.00001-20 wt %, and more preferably 0.00001-10 wt % based on the total weight of the cosmetic composition.

If the amount of senkyunolide A is lower than 0.00001 wt %, the aimed skin-whitening effect may be negligible; in the case of exceeding 20 wt %, some adverse effects such as skin irritation and instability in formulation is very likely to occur.

Furthermore, the cosmetic compositions of the present invention may contain auxiliaries as well as carrier in addition to senkyunolide A. The non-limiting examples of auxiliaries include preservatives, antioxidants, stabilizers, solubilizers, vitamins, colorants, odor improvers or mixtures of these ingredients.

The cosmetic compositions of this invention may be formulated in a wide variety of form, for non-limited example, including a solution, a suspension, an emulsion, a paste, an ointment, a gel, a cream, a lotion, a powder, a soap, a surfactant-containing cleanser, an oil, a powder foundation, an emulsion foundation, a wax foundation and a spray. In detail, the cosmetic composition of the present invention can be provided in a form of skin softener (skin lotion), astringent lotion, nutrient emulsion (milk lotion), nutrient cream, message cream, essence, eye cream, cleansing cream, cleansing foam, cleansing water, facial pack, spray or powder.

The cosmetically acceptable carrier contained in the present cosmetic composition, may be varied depending on the type of the formulation. For example, the formulation of ointment, pastes, creams or gels may comprise animal and vegetable fats, waxes, paraffins, starch, tragacanth, cellulose derivatives, polyethylene glycols, silicones, bentonites, silica, talc, zinc oxide or mixtures of these ingredients.

In the formulation of powder or spray, it may comprise lactose, talc, silica, aluminum hydroxide, calcium silicate, polyamide powder and mixtures of these ingredients. Spray may additionally comprise the customary propellants, for example, chlorofluorohydrocarbons, propane/butane or dimethyl ether.

The formulation of solution and emulsion may comprise solvent, solubilizer and emulsifier, for example water, ethanol, isopropanol, ethyl carbonate, ethyl acetate, benzyl alcohol, benzyl benzoate, propylene glycol, 1,3-butyleneglycol, oils, in particular cottonseed oil, groundnut oil, maize germ oil, olive oil, castor oil and sesame seed oil, glycerol fatty esters, polyethylene glycol and fatty acid esters of sorbitan or mixtures of these ingredients.

The formulation of suspension may comprise liquid diluents, for example water, ethanol or propylene glycol, suspending agents, for example ethoxylated isosteary alcohols, polyoxyethylene sorbitol esters and poly oxyethylene sorbitan esters, micocrystalline cellulose, aluminum metahydroxide, bentonite, agar and tragacanth or mixtures of these ingredients.

The formulation of cleansing compositions with surfactant may comprise aliphatic alcohol sulfate, aliphatic alcohol ether sulfate, sulfosucinnate monoester, isothinate, imidazolium derivatives, methyltaurate, sarcocinate, fatty acid amide ether sulfate, alkyl amido betain, aliphatic alcohol, fatty acid glyceride, fatty acid diethanolamlde, vegetable oil, lanoline derivatives, ethoxylated glycerol fatty acid ester or mixtures of these ingredients.

The following specific examples are intended to be illustrative of the invention and should not be construed as limiting the scope of the invention as defined by appended claims.

EXAMPLES

Materials

The roots from *Cnidium officinale* or *Ligusticum chuanxiong* employed for extraction and purification of senkyunolide A were purchased from Kyung-dong Oriental Medicine Market in Seoul, Korea.

Example I

Isolation and Purification of Senkyunolide A 3 kg of the dried root powders (from *Cnidium officinale* or *Ligusticum chuanxiong*) were immersed in 18 L of ethanol for 3-5 days, filtered through Whattman No. 5 paper filter and dried in a vacuous rotary evaporator equipped with cooling condenser. The dried powder obtained thus was fractionated in a mixture of ethylacetate and distilled water and the ethylacetate layer was evaporated under vacuum. The dried substance was loaded on an open silica column (normal hexane: ethylacetate=3:1) and the fraction with $R_f=0.5$ was collected and evaporated, thus yielding 30.1 g of product. The value of $R_f=0.5$ was pre-determined via prep-TLC with the control of senkyunolide A commercially available. Among the product, 3.1 g of senkyunolide A was finally purified through prep-LC, distillation under vacuum and removal of residual solvent using vacuum pump, consecutively:

Exact Mass: 192.12; ms (m/z (%)) 192(17.19), 163(1.91), 135(3.57), 107(100); $^1$HNMR 6.21(dt), 5.91(dt), 4.93(dd) 2.47-1.39(m), 0.9(t); IR 2932, 2872, 1747, 1241 cm$^{-1}$; UV (207, 278 nm)

Experimental Example I

Inhibitory Effect of Senkyunolide A on Melanocyte-Stimulating Hormone (MSH) and Resultant Melanie Synthesis The inhibitory effect of the senkyunolide A purified through the Example I on activity of MSH was tested as follows:

Melanocytes (mouse B-16 melanoma strain; ATCC CRL 6323) were purchased from ATCC (USA). The melanocytes were maintained in T-flask supplemented with DMEM containing 4.5 g/L glucose, 10% FBS (fetal bovine serum) and 1% penicillin-streptomycin in a humidified incubator supplied with 5% $CO_2$ at 37° C. After 24 h incubation, cells were detached by trypsinization and 5×10$^4$ cells were plated on each 100 mm plate supplemented with fresh medium. After additional incubation for 24 h, cells were pretreated with the senkyunolide A in a dose dependent manner (0, 5, 10, 20 and 50 μg/ml) and activated with 100 μM of α-melanocyte stimulating hormone (αMSH, Sigma, USA). The amount of melanin was measured after incubation for 5 days. Melanin samples were stirred in 5% trichloroacetate (TCA), centrifuged and rinsed with PBS. Precipitated melanin was resolved in 1N NaOH and absorbance was measured at 475 nm. Inhibitory potential of melanin synthesis was calculated based on standard curve acquired by synthetic melanin (Sigma, USA). The results are summarized in the following Table I:

TABLE I

| Conc. of Senkyunolide A (μg/ml) | Synthesis of Melanin (%) |
|---|---|
| 0* | 100.0 |
| 0** | 175.8 |
| 5** | 160.6 |
| 10** | 121.3 |
| 20** | 105.5 |
| 50** | 98.7 |

*MSH untreated
**MSH(100 μM) treated

As shown in Table I, senkyunolide A according to the present invention was found to decrease melanin synthesis of melanocytes induced by MSH in a dose dependent manner and 50 μg/ml of senkyunolide A inhibited the melanin synthesis to the level below the amount of MSH-uninduced melanocytes (100%). These data show the pivotal role of the senkyunolide A of the present invention in the inhibition of MSH activity and consequent melanin decrease.

Experimental Example II

Inhibitory Effect of Senkyunolide A on Tyrosinase Expression

Melanocyts were plated in the same manner as Experiment Example I, pretreated with senkyunolide A in a dose dependent manner (0, 5, 10, 20 and 50 μg/ml) and activated with 100 μl of α-melanocyte stimulating hormone. Melanocytes were harvested after 3 days incubation. The harvested cells were rinsed twice in PBS and ultrasonicated in 0.1% Triton X-100 for 30 seconds. Cell debris was separated from supernatant by high speed centrifugation (12,000 rpm, 30 mins, 4° C.). Proteins in supernatant were separated by electrophoresis, the gels were reacted in 0.2% dopa solution for 8 h and the level of tyrosinase was measured. The results are summarized in the following Table II:

TABLE II

| Conc. Of Senkyunolide A (μg/ml) | Tyrosinae band intensity |
|---|---|
| 0* | 100.0 |
| 0** | 205.0 |
| 5** | 185.0 |
| 10** | 153.0 |
| 20** | 132.0 |
| 50** | 101.0 |

*MSH untreated
**MSH(100 μM) treated

As shown in Table II, senkyunolide A of the present invention was found to decrease the tyrosinase expression in melanocytes in a dose dependent manner and 50 μg/ml senkyunolide A caused the similar band intensity to tyrosinase of MSH-uninduced melanocytes. These data show the enhanced inhibitory effect of the senkyunolide A on melanin synthesis.

From the results of Experimental Examples I and II, it will be appreciated that the inhibitory action of senkyunolide A in signal transduction cascade for melanin synthesis occurs further upstream, i.e., at MSH than conventional whitening agents of which target is tyrosinase. Therefore, senkyunolide A of this invention is very likely to exhibit improved whitening effect and to show the similar effect to conventional whitening agents even in lower level.

Formulation Examples

The formulations of the present invention can be provided in a form of skin softener (skin lotion), astringent lotion, nutrient emulsion (milk lotion), nutrient cream, message cream, essence, facial pack without limiting the applicable formulations therein.

Formulation I: Skin Lotion (Skin Softener)

One example of skin lotion containing senkyunolide A according to the present invention is formulated as below:

TABLE III

| Ingredients | Amount (wt %) |
|---|---|
| Senkyunolide A | 1.0 |
| Glycerine | 5.0 |
| 1,3-butylglycol | 3.0 |
| PEG 150 | 1.0 |
| Alantoine | 0.1 |
| DL-pantenol | 0.3 |
| EDTA-2Na | 0.02 |
| Benzophenon-9 | 0.04 |
| Sodium hyaluronate | 5.0 |
| Ethanol | 10.0 |
| Octyldodeces-16 | 0.2 |
| Polysorbate 20 | 0.2 |
| Antiseptic, fragrant, colorant | Small amount |
| DW | To be total |
| Total | 100 |

Formulation II: Astringent Lotion

One example of the astringent lotion containing senkyunolide A of the present invention is formulated as below Table IV:

TABLE IV

| Ingredients | Amount (wt %) |
| --- | --- |
| Senkyunolide A | 1.0 |
| Glycerine | 2.0 |
| 1,3-butylglycol | 2.0 |
| Alantoine | 0.2 |
| DL-pantenol | 0.2 |
| EDTA-2Na | 0.02 |
| Benzophenon-9 | 0.04 |
| Sodium hyaluronate | 3.0 |
| Ethanol | 15.0 |
| Polysorbate 20 | 0.3 |
| Witchhazel extract | 2.0 |
| Citric acid | Small amount |
| Antiseptic, fragrant, colorant | Small amount |
| DW | To be total |
| Total | 100 |

Formulation III: Nutrient Emulsion (Milk Lotion)

One example of the nutrient emulsion containing senkyunolide A of the present invention is formulated as below Table V:

TABLE V

| Ingredients | Amount (wt %) |
| --- | --- |
| Senkyunolide A | 1.5 |
| Glyceryl stearate SE | 1.5 |
| Stearyl alcohol | 1.5 |
| Lanoline | 1.5 |
| Polysorbate 60 | 1.3 |
| Sorbitan stearate | 0.5 |
| Hydrogenated vegetable oil | 1.0 |
| Mineral oil | 5.0 |
| Squalane | 3.0 |
| Trioctanoine | 2.0 |
| Dimethicon | 0.8 |
| Tocopherol acetate | 0.5 |
| Carboxyvinyl polymer | 0.12 |
| Glycerine | 5.0 |
| 1,3-butylglycol | 3.0 |
| Sodium hyaluronate | 5.0 |
| Tri-ethanolamine | 0.12 |
| Antiseptic, fragrant, colorant | Small amount |
| DW | To be total |
| Total | 100 |

Formulation IV: Nutrient Cream

One example of nutrient cream containing senkyunolide A of the present invention is formulated as below Table VI:

TABLE VI

| Ingredients | Amount (wt %) |
| --- | --- |
| Senkyunolide A | 5.0 |
| Lypophilic glycerol monostearate | 2.0 |
| Cetearyl alcohol | 2.2 |
| Stearic acid | 1.5 |
| Wax | 1.0 |
| Polysorbate 60 | 1.5 |
| Sorbitan stearate | 0.6 |
| Hydrogenated vegetable oil | 1.0 |
| Squalane | 3.0 |
| Mineral oil | 5.0 |
| Trioctanoine | 5.0 |
| Dimethicon | 1.0 |
| Sodium magnesium silicate | 0.1 |
| Glycerine | 5.0 |
| Betaine | 3.0 |

TABLE VI-continued

| Ingredients | Amount (wt %) |
| --- | --- |
| Tri-ethanolamine | 1.0 |
| Sodium hyaluronate | 4.0 |
| Antiseptic, fragrant, colorant | Small amount |
| DW | To be total |
| Total | 100 |

Formulation V: Message Cream

One example of message cream containing senkyunolide A of the present invention is formulated as below Table VII:

TABEL VII

| Ingredients | Amount (wt %) |
| --- | --- |
| Senkyunolide A | 1.0 |
| Lypophilic glycerol monostearate | 1.5 |
| Stearyl alcohol | 1.5 |
| Stearic acid | 1.0 |
| Polysorbate 60 | 1.5 |
| Sorbitan stearate | 0.6 |
| Isostearyl isostearate | 5.0 |
| Squalane | 5.0 |
| Mineral oil | 35.0 |
| Dimethicon | 0.5 |
| Hydroxyethyl cellulose | 0.12 |
| Glycerine | 6.0 |
| Tri-ethanolamine | 0.7 |
| Antiseptic, fragrant, colorant | Small amount |
| DW | To be total |
| Total | 100 |

Formulation VI: Essence

One example of essence containing senkyunolide A of the present invention is formulated as below Table VIII:

TABLE VIII

| Ingredients | Amount (wt %) |
| --- | --- |
| Senkyunolide A | 1.5 |
| Glycerine | 10.0 |
| Betaine | 5.0 |
| PEG 1500 | 2.0 |
| Alantoine | 0.1 |
| DL-pantenol | 0.3 |
| EDTA-2Na | 0.02 |
| Benzophenon-9 | 0.04 |
| Hydroxyethyl cellulose | 0.1 |
| Sodium hyaluronate | 8.0 |
| Carboxyvinyl polymer | 0.2 |
| Triethanolamine | 0.18 |
| Octyldodecanol | 0.3 |
| Octyldodeces-16 | 0.4 |
| Ethanol | 6.0 |
| Antiseptic, fragrant, colorant | Small amount |
| DW | To be total |
| Total | 100 |

Formulation VII: Facial Pack

One example of facial pack containing senkyunolide A of the present invention is formulated as below Table IX:

TABLE IX

| Ingredients | Amount (wt %) |
|---|---|
| Senkyunolide A | 1.0 |
| Polyvinyl alcohol | 15.0 |
| Cellulose gum | 0.15 |
| Glycerine | 3.0 |
| PEG 1500 | 2.0 |
| Cyclodextrin | 0.15 |
| DL-pantenol | 0.4 |
| Alantoine | 0.1 |
| Monoammonium glycyrrhizinate | 0.3 |
| Nicotineamide | 0.5 |
| Ethanol | 6.0 |
| PEG 40 hydrogenated castor oil | 0.3 |
| Antiseptic, fragrant, colorant | Small amount |
| DW | To be total |
| Total | 100 |

Experiment 3: Skin-Whitening Efficacy of the Cosmetic Compositions of the Present Invention The skin-whitening efficacy of the cosmetic compositions of the present invention was evaluated by practical use. The nutrient cream, containing 1.5% senkyunolide A, described in the Formulation IV was employed and senkyunolide A was substituted with the same amount of DW for control in this trial.

At first, 20 women aged from 30 to 40 were caused skin-pigmentation by UV irradiation. Their randomized 2 groups were applied with the nutrient cream of the Formulation IV or its control cream. The application in upper arms lasted for 2 months with diurnal twice applications in every morning and night. Whitening efficacy was evaluated by observation compared to control groups. The results are summarized in the following Table X:

TABLE X

| | Effective | Moderately effective | Ineffective | Efficacy (%) |
|---|---|---|---|---|
| Formulation IV | 41 | 6 | 3 | 94.0 |
| Control | 5 | 12 | 33 | 34.0 |

As shown in Table X, the Formulation IV according to the present invention shows significantly enhanced whitening effect compared to its control formulation. Furthermore, there was no skin trouble in any testee.

Having described preferred embodiments of the present invention, it is to be understood that variants and modifications thereof falling within the spirit of the invention may become apparent to those skilled in this art, and the scope of this invention is to be determined by appended claims and their equivalents.

What is claimed is:

1. A method for inhibiting melanocyte-stimulating hormone(MSH) comprising applying a composition comprising an active agent consisting of senkyunolide A, said active agent being present in an amount of 0.00001 to 20 wt % based on the total weight of the composition, wherein said senkyunolide A is purified senkyunolide A or chemically synthesized senkyunolide A.

2. The method according to claim 1, wherein the senkyunolide A is purified from *Cnidium officinale* or *Ligusticum chuanxiong*.

3. The method according to claim 1, wherein the senkyunolide A is chemically synthesized.

4. The method according to claim 1, wherein the composition is in the form of one selected from a solution, a suspension, an emulsion, a paste, an ointment, a gel, a cream, a lotion, a powder, a soap, a surfactant-containing cleanser, an oil, a powder foundation, an emulsion foundation, a wax foundation and a spray.

* * * * *